United States Patent [19]

Hill et al.

[11] 4,334,544
[45] Jun. 15, 1982

[54] EAR LOBE CLIP WITH HEART BEAT SENSOR

[75] Inventors: Loran R. Hill, Olney, Ill.; Steven E. Titcomb, Milton, Mass.

[73] Assignee: AMF Incorporated, White Plains, N.Y.

[21] Appl. No.: 144,720

[22] Filed: Apr. 28, 1980

[51] Int. Cl.³ .............................................. A61B 5/02
[52] U.S. Cl. .................................... 128/664; 128/666; 128/687
[58] Field of Search ............... 128/633, 664, 665, 666, 128/667, 687, 689, 789; 179/107 H

[56] References Cited

U.S. PATENT DOCUMENTS

| | | | |
|---|---|---|---|
| 2,414,747 | 1/1947 | Kirshbaum | 128/633 X |
| 3,051,165 | 8/1962 | Kompelien | 128/667 |
| 3,192,921 | 7/1965 | Erickson et al. | 128/667 |
| 3,810,460 | 5/1974 | Nie | 128/666 |
| 3,815,583 | 6/1974 | Scheidt | 128/666 |

*Primary Examiner*—Lee S. Cohen

*Attorney, Agent, or Firm*—David E. Dougherty; Walter Lewis

[57] ABSTRACT

A pair of generally parallel spaced plastic arms are pivoted to each other at their central portions by interleaved pairs of tabs having a pivot pin extending therethrough. A light coil spring on the pivot pin biases one pair of opposite ends of the arms into light engagement for clipping them on to an ear lobe. The one pair of opposite ends have a pair of hollow bosses formed thereon, with heart beat sensors positioned in each boss. Electric wires connected to the sensors extend therefrom along the arms through channels formed in the arms. The pivot pin has heads formed at its opposite ends. Apertures are formed in these heads and an elongated strip of plastic material has its opposite ends positioned in the apertures so that the remainder of the strip of material comprises an open loop for hanging the arms off the ear of the lobe to which the arms are clipped. The strip of material has a friction fit in the apertures so the size of the loop can be adjusted by selectively pulling the ends of the strip through the apertures.

3 Claims, 4 Drawing Figures

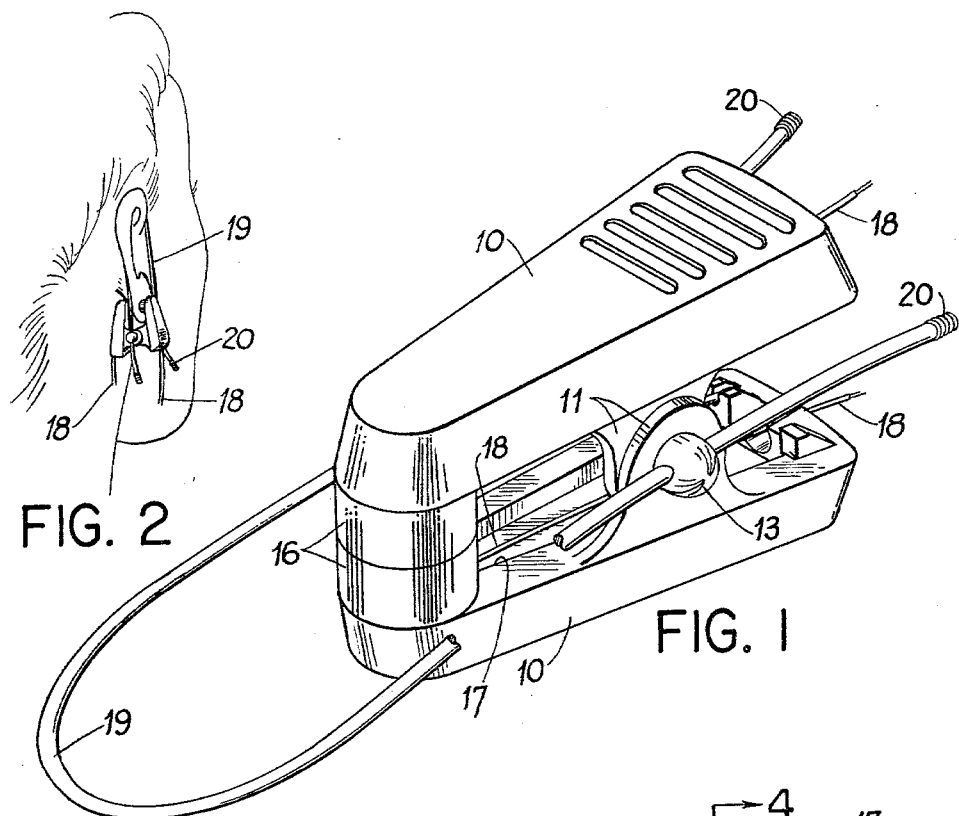
FIG. 2
FIG. 1
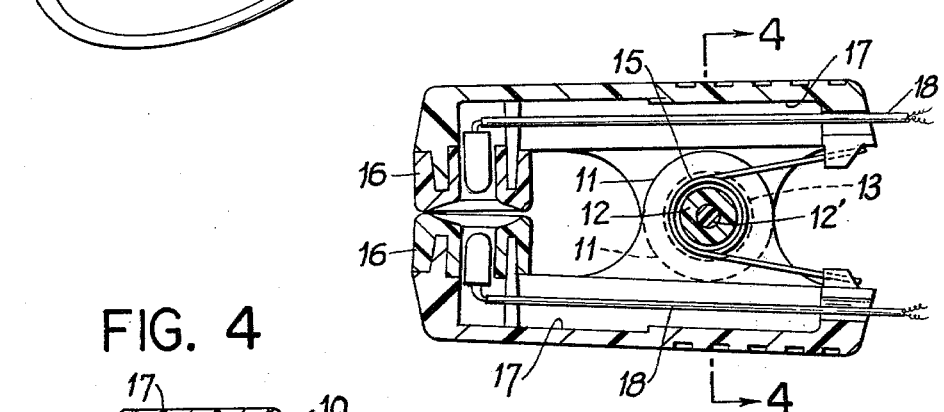
FIG. 3
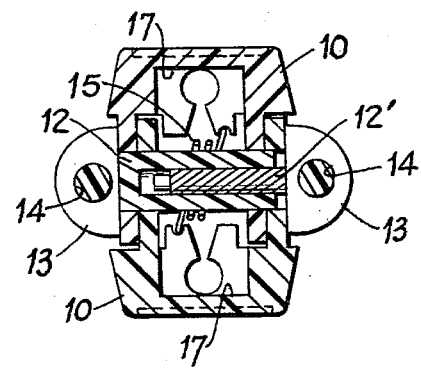
FIG. 4

EAR LOBE CLIP WITH HEART BEAT SENSOR

This invention relates to an ear clip heart monitor, and more particularly to a low cost, minimum parts ear lobe clip heart monitor which is very comfortable for the user.

In the prior art ear clip heart monitors have an infra-red light source cell on one side and a photo-electric sensor cell on the other side. This clips on to the ear lobe. The light source illuminates the flesh at the ear lobe, and the sensor detects the variation in density due to the infusion of blood during heart beats.

Typically these devices are wired back to a control, such as on an exercise device, to give a read out of the heart beat while a person is exercising. Because of the wires, movements of the person, and weight of the clip, the clamping forces of the clip must be quite high in order to hold the clip on the user's ear lobe. Otherwise, the clip will be pulled or fall off the ear lobe. Of course, the needed high clamping force make the clip rather uncomfortable to the exerciser.

Briefly, in the instant invention only a light spring is used for the clip per se which is just sufficient to obtain good contact of the light and sensor cells with the ear lobe. The weight of the clip or the force of any pulls imposed on the clip however are not borne by the ear lobe. Rather, these are transferred from the ear lobe to the ear itself by an adjustable loop that hangs the ear lobe clip off the ear.

The invention will be best understood by considering the following description and accompanying drawings in which FIG. 1 is a perspective view of the device, FIG. 2 shows the same on the ear of a user, and FIGS. 3 and 4 are additional views of the device to further show its internal parts.

As shown in the drawings, the clip comprises a pair of plastic arms 10 which are identical and are pivoted to each other at their central parts. Each arm has a pair of spaced apertured pivot tabs 11. These tabs 11 are interleaved and a hinge pin 12 holds the tabs together. The hinge pin 12 is hollow and receives a lock pin 12' therein. The outer ends of the pins 12, 12' are provided with heads 13 which have apertures 14 formed therein. A light spring 15 surrounds the pins 12, 12' with opposite ends thereof bearing against the insides of arms 10, at the right hand end of arms 10 when viewing FIG. 1, to bias their left hand ends towards each other.

The left hand ends of the arms 10, when viewing FIG. 1, have integral hollow protuberances or bosses 16, thereon which will butt up against each other because of the bias spring 15. These bosses 16 are hollow for the purpose of receiving the not shown but previously mentioned light source and sensor cells, one on each side. The insides of the arms 10 have integral lengthwise extending channels 17 formed therein which communicate with the interior of the bosses 16. This is for the purpose of bringing wires 18 connected to cells out from the ear clip, see FIG. 2. Wires 18 extend down along the head of the user for ultimate connection to a control or heart beat read out on an exercise device, which could be a not shown exercise bicycle.

As shown, the ear clip is actually hung off the user's ear by a loop 19. Loop 19 comprises a length of hollow, flexible, plastic tubing which has an OD slightly larger than the ID of the holes 14 in heads 13. So, when the tube 19 is inserted into the holes 14 it has a sliding friction fit therein in order to adjust the size of the loop. The outer ends of the tube 19 are fitted with plugs 20 to slightly enlarge the same so that they can't be accidentally pulled through the heads 13.

The spring 15 is a very light one which is just sufficient to butt the two bosses 16 together or in light contact with the ear lobe. After the clip is clipped on to the ear lobe the loop 19 is looped over the ear and the opposite ends of the tube 19 pulled through the heads 13 to close the loop 19 on the ear so in fact all the forces on the clip due to the weight thereof, the wires 18, and movements of the user, are imposed on the ear and not its lobe. This makes the device very comfortable for the user, but still it will not pull loose off the ear lobe.

We claim:

1. An ear lobe clip with heart beat sensor means therein, comprising a pair of equal length plastic material pivot arms, said pair of arms facing each other in spaced and generally parallel relationship, said pair of arms having a pivotal connection with each other at their respective central portions for pivotal movement of each of their two pairs of opposite ends towards and away from each other, a spring at said pivotal connection, said spring being operative to bias one of said pair of opposite ends into light engagement with each other for clipping said one pair of opposite ends on to an ear lobe, heart beat sensor means at each of said one pair of opposite ends, wires electrically connected to each of said sensor means and extending along said arms and out therefrom at the other pair of opposite ends of said arms, adjustable means for hanging said arms off the ear of the lobe to which said arms are clipped, said adjustable means comprising a pair of apertures formed on said arms, a flexible strip of plastic material, opposite ends of said strip extending into said apertures whereby the remainder of said strip comprises an open loop for hanging said arms on said ear, and said strip opposite ends having a friction fit in said apertures to pull said opposite strip ends in either direction through said apertures to adjustably set the size of said loop.

2. In an ear lope clip with heartbeat sensor means as in claim 1, said pivotal connection comprising a pair of integral spaced tabs on the central portion of each of said arms, said pairs of tabs being interleaved with each other and pivot pin means extending therethrough, a pair of integral hollow bosses formed at said one pair of opposite ends, said sensor means being positioned in said bosses, lengthwise extending channels formed in the opposite inner facing sides of said arms, said channels being in communication with the interior of said bosses and said wires extending from said sensor means along said arms in said channels, and said spring being coiled about said pivot pin means and having its opposite ends bearing against said other pair of opposite ends to bias said one pair of opposite ends towards each other.

3. In an ear lobe clip with heartbeat sensor means as in claim 2, said pivot pin means having a head formed at opposite ends thereof, said apertures being formed in said heads, and said flexible strip of plastic material comprising an elongated small diameter hollow plastic tube, and the outer dimension of said hollow tube being slightly oversize with respect to the size of said apertures to provide an adjustable friction fit therein.

* * * * *